United States Patent [19]

Coppi

[11] 4,225,335
[45] Sep. 30, 1980

[54] DIOXOLANE SUBSTITUTED ACETANILIDS

[75] Inventor: Deborah L. Coppi, Chicago, Ill.

[73] Assignee: Velsicol Chemical Corporation, Chicago, Ill.

[21] Appl. No.: 50,835

[22] Filed: Jun. 21, 1979

[51] Int. Cl.³ .................. C07D 13/04; A01N 9/20
[52] U.S. Cl. ........................ 71/88; 260/340.9 R
[58] Field of Search ............ 260/340.9 R; 71/88

[56] References Cited

U.S. PATENT DOCUMENTS

| | | | |
|---|---|---|---|
| 3,859,308 | 1/1975 | Richter et al. | 71/88 |
| 3,946,044 | 3/1976 | Richter et al. | 260/340.9 |
| 3,946,045 | 3/1976 | Richter et al. | 260/340.9 R |
| 3,948,950 | 4/1976 | Richter et al. | 260/338 |
| 4,113,464 | 9/1978 | Stach et al. | 260/340.9 R |

Primary Examiner—Donald G. Daus
Assistant Examiner—James H. Turnipseed
Attorney, Agent, or Firm—Dietmar Olesch; Robert J. Schwarz

[57] ABSTRACT

This invention discloses new chemical compounds of the formula

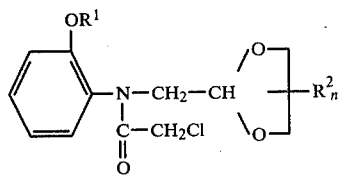

wherein $R^1$ and $R^2$ are each independently methyl, ethyl or propyl and n is the integer 1 or 2.

The subject compounds are useful as herbicides.

10 Claims, No Drawings

DIOXOLANE SUBSTITUTED ACETANILIDS

This invention relates to new compositions of matter and more particularly relates to new chemical compounds of the formula

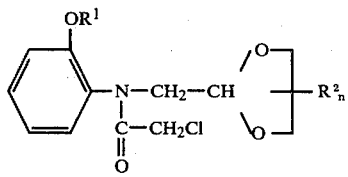

where $R^1$ is alkyl; $R^2$ is methyl, ethyl or propyl; and n is the integer 1 or 2.

In a preferred embodiment of the present invention $R^1$ is alkyl containing from 1 to 6 carbon atoms.

The compounds of the present invention are useful as herbicides.

The compounds of this invention can be prepared by reacting a substituted aniline of the formula

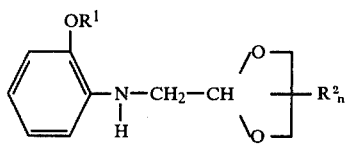

wherein $R^1$, $R^2$ and n are as heretofore described, with chloroacetyl chloride. This reaction can be effected by combining a solution of the compound of formula II in diethyl ether with chloroacetyl chloride in the presence of an acid acceptor such as an alkali metal carbonate or bicarbonate at a temperature of $-10°$ C. to about 20° C. The acid acceptor can be conveniently dissolved in water. The reaction mixture is stirred during the addition of chloroacetyl chloride. After the reaction is completed, the organic phase can be separated from the aqueous phase and filtered. The filtrate can then be washed with aqueous sodium carbonate, dried and stripped of solvent to yield the desired product. This product can be used as such or can be further purified by conventional means.

The compounds of formula II can be prepared by reacting an aniline of the formula

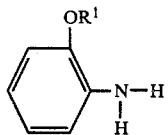

wherein $R^1$ is as heretofore described, with a compound of the formula

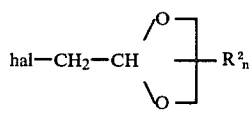

wherein hal designates halogen, preferably bromine, and $R^2$ and n are as heretofore described. This reaction can be effected by combining the reactants in the presence of an acid acceptor such as an alkali metal carbonate and heating the mixture at a temperature of from 80° to 120° C. for a period of from about one to about four hours. After this time the desired product can be recovered by distillation.

The compounds of formula II, useful for preparing the compounds of the present invention, are 2-methoxyaniline, 2-ethoxyaniline, 2-propoxyaniline, 2-butoxyaniline, 2-pentoxyaniline and 2-hexyloxyaniline.

Exemplary compounds of formula III, useful in preparing the compound of this invention are 2-bromomethyl-4-methyl-1,3-dioxolane, 2-bromomethyl-4-ethyl-1,3-dioxolane, 2-bromomethyl-4-propyl-1,3-dioxolane, 2-bromomethyl-4,5-dimethyl-1,3-dioxolane, 2-bromomethyl-4,5-diethyl-1,3-dioxolane, 2-bromomethyl-4-methyl-5-ethyl-1,3-dioxolane and the like.

The manner in which the compounds of the present invention can be prepared is more specifically illustrated in the following examples.

EXAMPLE 1

Preparation of N-(4,5-Dimethyl-1,3-dioxolan-2-ylmethyl)-2-methoxyaniline

2-Methoxyaniline (87 ml; 0.7 mole) and sodium carbonate (31.66 grams) were charged into a glass reaction vessel equipped with a mechanical stirrer, thermometer and reflux condenser. 2-Bromomethyl-4,5-dimethyl-1,3-dioxolane (25 mls) was added and the reaction mixture was heated at a temperature of 100° C. for a period of about 4 hours. After this time the reaction mixture was filtered and additional sodium carbonate (5.00 grams) was added to the filtrate. The mixture was then distilled under reduced pressure to yield the desired product N-(4,5-dimethyl-1,3-dioxolan-2-ylmethyl)-2-methoxyaniline boiling at 125° to 128° C. at 0.1 mm of Hg pressure.

EXAMPLE 2

Preparation of N-(4,5-Dimethyl-1,3-dioxolan-2-ylmethyl)-2-methoxy-α-chloroacetanilide N-(4,5-Dimethyl-1,3-dioxolan-2-ylmethyl)-2-methoxyaniline (5.21 grams), diethyl ether (30 ml), sodium carbonate (4.66 grams) and water (50 ml) were charged into a glass reaction flask equipped with stirrer, thermometer and cooling means. The mixture was cooled to a temperature of 0° to 5° C. and chloroacetyl chloride (2 ml) was slowly added with stirring. After the addition was completed, the mixture was stirred for a period of 1 hour. After this time the organic phase was separated from the aqueous phase and filtered. The filtrate was washed with aqueous sodium carbonate three times and then dried over anhydrous magnesium sulfate. The dried solution was filtered and stripped of solvent under reduced pressure to yield the desired product N-(4,5-dimethyl-1,3-dioxolan-2-ylmethyl)-2-methoxy-α-chloroacetanilide as a white crystalline solid having a melt point of 72° to 73° C.

EXAMPLE 3

Preparation of N-(4,5-Dimethyl-1,3-dioxolan-2-ylmethyl)-2-ethoxyaniline

Ethoxyaniline (44.5 ml) and sodium carbonate (31.6 grams) were charged into a glass reaction vessel equipped with a mechanical stirrer, thermometer and reflux condenser. 2-Bromomethyl-4,5-dimethyl-1,3-dioxolane (25 ml) was added over a period of 1 hour and the reaction mixture was heated at reflux for a period of 1 hour after the addition was completed. After this time the reaction mixture was filtered and additional sodium carbonate was added to the filtrate. The mixture was then distilled under reduced pressure to yield the desired product N-(4,5-dimethyl-1,3-dioxolan-2-ylmethyl)-2-ethoxyaniline boiling at 123° C. at 0.01 mm of Hg pressure.

EXAMPLE 4

Preparation of N-(4,5-Dimethyl-1,3-dioxolan-2-ylmethyl)-2-ethoxy-α-chloroacetanilide N-(4,5-Dimethyl-1,3-dioxolan-2-ylmethyl)-2-ethoxyaniline (5.41 ml; 0.022 mole), diethyl ether (30 ml), sodium carbonate (4.66 grams) and water (50 ml) were charged into a glass reaction vessel equipped with stirrer, thermometer and cooling means. The mixture was cooled to a temperature of 4° to 6° C. and chloroacetyl chloride (2.71 ml) was slowly added with stirring. After the addition was completed stirring was continued for a period of 1 hour. After this time the organic phase was separated from the aqueous phase and filtered. The filtrate was then washed with aqueous sodium carbonate and thereafter dried over anhydrous magnesium sulfate. The dried solution was filtered and stripped of solvent under reduced pressure to yield the desired product N-(4,5-dimethyl-1,3-dioxolan-2-ylmethyl)-2-ethoxy-α-chloroacetanilide as a white solid having a melt point of 43.0° C.

EXAMPLE 5

Preparation of N-(4-Ethyl-1,3-dioxolan-2-ylmethyl)-2-methoxyaniline

2-Methoxyaniline (0.5 mole) and sodium carbonate (30 grams) are charged into a glass reaction vessel equipped with a mechanical stirrer, thermometer and reflux condenser. 2-Bromomethyl-4-ethyl-1,3-dioxolane (0.55 mole) is slowly added and the reaction mixture is heated at reflux for a period of about 1 hour. After this time the reaction mixture is filtered and additional sodium carbonate (5 grams) is added to the filtrate. The mixture is then distilled under reduced pressure to yield the desired product N-(4-ethyl-1,3-dioxolan-2-ylmethyl)-2-methoxyaniline.

EXAMPLE 6

Preparation of N-(4-Ethyl-1,3-dioxolan-2-ylmethyl)-2-methoxy-α-chloroacetanilide N-(4-Ethyl-1,3-dioxolan-2-ylmethyl)-2-methoxyaniline (0.25 mole), diethyl ether (30 ml), sodium carbonate (35.5 grams) and water (50 ml) are charged into a glass reaction vessel equipped with stirrer, thermometer and cooling means. The mixture is cooled to about 5° C. and chloroacetyl chloride (0.28 mole) is added dropwise with stirring. After the addition is completed, stirring is continued for 1 hour. After this time the organic phase is separated from the aqueous phase and is filtered. The filtrate is then washed with aqueous sodium carbonate, dried over anhydrous magnesium sulfate and filtered. The filtrate is then stripped of solvent under reduced pressure to yield the desired product N-(4-ethyl-1,3-dioxolan-2-ylmethyl)-2-methoxy-α-chloroacetanilide as the residue.

EXAMPLE 7

Preparation of N-(4-Propyl-1,3-dioxolan-2-ylmethyl)-2-methoxyaniline

2-Methoxyaniline (0.05 mole) and sodium carbonate (30 grams) are charged into a glass reaction vessel equipped with a mechanical stirrer, thermometer and reflux condenser. 2-Bromomethyl-4-propyl-1,3-dioxolane (0.55 mole) is slowly added and the reaction mixture is heated at reflux for a period of about 1 hour. After this time the reaction mixture is filtered and additional sodium carbonate (5 grams) is added to the filtrate. The mixture is then distilled under reduced pressure to yield the desired product N-(4-propyl-1,3-dioxolan-2-ylmethyl)-2-methoxyaniline.

EXAMPLE 8

Preparation of N-(4-Propyl-1,3-dioxolan-2-ylmethyl)-2-methoxy-α-chloroacetanilide N-(4-Propyl-1,3-dioxolan-2-ylmethyl)-2-methoxyaniline (0.25 mole), diethyl ether (30 ml), sodium carbonate (35.5 grams) and water (50 ml) are charged into a glass reaction vessel equipped with stirrer, thermometer and cooling means. The mixture is cooled to about 5° C. and chloroacetyl chloride (0.28 mole) is added dropwise with stirring. After the addition is completed, stirring is continued for 1 hour. After this time the organic phase is separated from the aqueous phase and is filtered. The filtrate is then washed with aqueous sodium carbonate, dried over anhydrous magnesium sulfate and filtered. The filtrate is then stripped of solvent under reduced pressure to yield the desired product N-(4-propyl-1,3-dioxolan-2-ylmethyl)-2-methoxy-α-chloroacetanilide as the residue.

EXAMPLE 9

Preparation of N-(4-Methyl-5-ethyl-1,3-dioxolan-2-ylmethyl)-2-methoxyaniline

2-Methoxyaniline (0.05 mole) and sodium carbonate (30 grams) are charged into a glass reaction vessel equipped with a mechanical stirrer, thermometer and reflux condenser. 2-Bromomethyl-4-methyl-5-ethyl-1,3-dioxolane (0.55 mole) is slowly added and the reaction mixture is heated at reflux for a period of about 1 hour. After this time the reaction mixture is filtered and additional sodium carbonate (5 grams) is added to the filtrate. The mixture is then distilled under reduced pressure to yield the desired product N-(4-methyl-5-ethyl-1,3-dioxolan-2-ylmethyl)-2-methoxyaniline.

EXAMPLE 10

Preparation of N-(4-Methyl-5-ethyl-1,3-dioxolan-2-ylmethyl)-2-methoxy-α-chloroacetanilide N-(4-Methyl-5-ethyl-1,3-dioxolan-2-ylmethyl)-2-methoxyaniline (0.25 mole), diethyl ether (30 ml), sodium carbonate (35.5 grams) and water (50 ml) are charged into a glass reaction vessel equipped with stirrer, thermometer and cooling means. The mixture is cooled to about 5° C. and chloroacetyl chloride (0.28 mole) is added dropwise with stirring. After the addition is completed, stirring is continued for 1 hour. After this time the organic phase is separated from the aqueous phase and is filtered. The filtrate is then washed with aqueous sodium carbonate, dried over anhydrous magnesium sulfate and filtered. The filtrate is then stripped of solvent under reduced pressure to yield the desired product N-(4-methyl-5-ethyl-1,3-dioxolan-2-ylmethyl)-2-methoxy-α-chloroacetanilide as the residue.

EXAMPLE 11

Preparation of N-(4,5-Dimethyl-1,3-dioxolan-2-ylmethyl)-2-propoxyaniline

2-Propoxyaniline (0.5 mole) and sodium carbonate (30 grams) are charged into a glass reaction vessel equipped with a mechanical stirrer, thermometer and reflux condenser. 2-Bromomethyl-4,5-dimethyl-1,3-dioxolane (0.55 mole) is slowly added and the reaction mixture is heated at reflux for a period of about 1 hour. After this time the reaction mixture is filtered and additional sodium carbonate (5 grams) is added to the filtrate. The mixture is then distilled under reduced pressure to yield the desired product N-(4,5-dimethyl-1,3-dioxolan-2-ylmethyl)-2-propoxyaniline.

EXAMPLE 12

Preparation of N-(4,5-Dimethyl-1,3-dioxolan-2-ylmethyl)-2-propoxy-α-chloroacetanilide N-(4,5-dimethyl-1,3-dioxolan-2-ylmethyl)-2-propoxyaniline (0.25), diethyl ether (30 ml), sodium carbonate (35.5 grams) and water (50 ml) are charged into a glass reaction vessel equipped with stirrer, thermometer and cooling means. The mixture is cooled to about 50° C. and chloroacetyl chloride (0.28 mole) is added dropwise with stirring. After the addition is completed stirring is continued for 1 hour. After this time the organic phase is separated from the aqueous phase and is filtered. The filtrate is then washed with aqueous sodium carbonate, dried over anhydrous magnesium sulfate and filtered. The filtrate is then stripped of solvent under reduced pressure to yield the desired product N-(4,5-dimethyl-1,3-dioxolan-2-ylmethyl)-2-propoxy-α-chloroacetanilide as the residue.

EXAMPLE 13

Preparation of N-(4,5-Dimethyl-1,3-dioxolan-2-ylmethyl)-2-n-butoxyaniline 2-n-Butoxyaniline (99 grams; 0.6 moles) and sodium carbonate (31.6 grams) were charged into a glass reaction vessel equipped with a mechanical stirrer, thermometer and reflux condenser. 2-Bromomethyl-4,5-dimethyl-1,3-dioxolane (25 ml) was added and the reaction mixture was heated at a temperature of about 100° C. for a period of about 4 hours. After this time the reaction mixture was filtered and additional sodium carbonate (5.0 grams) was added to the filtrate. The mixture was then vacuum distilled and the fraction boiling at 123° C. and 0.05 mm of Hg pressure was collected to yield the desired product N-(4,5-dimethyl-1,3-dioxolan-2-ylmethyl)-2-n-butoxyaniline.

EXAMPLE 14

Preparation of N-(4,5-Dimethyl-1,3-dioxolan-2-ylmethyl)-2-n-butoxy-α-chloroacetamide N-(4,5-Dimethyl-(1,3-dioxolan-2-ylmethyl)-2-n-butoxyaniline (0.02 mole), diethyl ether (50 ml), sodium carbonate (4.66 grams) and water (30 ml) were charged into a glass reaction vessel equipped with stirrer, thermometer and cooling means. The mixture was cooled to a temperature of 0° to 5° C. and chloroacetyl chloride (0.22 moles) was slowly added with stirring. After the addition was completed, the mixture was stirred for a period of about 1 hour. After this time the organic phase was separated from the aqueous phase and filtered. The filtrate was washed with aqueous sodium carbonate and dried over anhydrous magnesium sulfate. The dried solution was filtered and stripped of solvent under reduced pressure to yield the desired product N-(4,5-dimethyl-1,3-dioxolan-2-ylmethyl)-2-n-butoxy-α-chloroacetamide as a solid melting at 28° C.

EXAMPLE 15

Preparation of N-(4-Methyl-1,3-dioxolan-2-ylmethyl)-2-methoxyaniline

2-Methoxyaniline (99 grams; 0.6 moles) and sodium carbonate (31.6 grams) were charged into a glass reaction vessel equipped with a mechanical stirrer, thermometer and reflux condenser. 2-Bromomethyl-4-methyl-1,3-dioxolane (25 ml) was added and the reaction mixture was heated at a temperature of about 100° C. for a period of about 4 hours. After this time the reaction mixture was filtered and additional sodium carbonate (5.0 grams) was added to the filtrate. The mixture was then vacuum distilled and the fraction boiling at 120° C. and 0.07 mm of Hg pressure was collected to yield the desired product N-(4-methyl-1,3-dioxolan-2-ylmethyl)-2-methoxyaniline.

EXAMPLE 16

Preparation of N-(4-Methyl-1,3-dioxolan-2-ylmethyl)-2-methoxy-α-chloroacetamide

N-(4-Methyl-1,3-dioxolan-2-ylmethyl)-2-methoxyaniline (0.02 mole), diethyl ether (50 ml), sodium carbonate (4.66 grams) and water (30 ml) were charged into a glass reaction vessel equipped with stirrer, thermometer and cooling means. The mixture was cooled to a temperature of 0° to 5° C. and chloroacetyl chloride (0.22 moles) was slowly added with stirring. After the addition was completed, the mixture was stirred for a period of about 1 hour. After this time the organic phase was separated from the aqueous phase and filtered. The filtrate was washed with aqueous sodium carbonate and dried over anhydrous magnesium sulfate. The dried solution was filtered and stripped of solvent under reduced pressure to yield the desired product N-(4-methyl-1,3-dioxolan-2-ylmethyl)-2-methoxy-α-chloroacetamide.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatomospheric pressure as aerosols. However, preferred liquid herbicidal compositions are emulsifiable concentrates which comprise an active compound according to this invention and as the inert carrier a solvent and an emulsifier. Such emulsifiable concentrates can be extended with water and/or oil to any desired concentration of active compound for application as sprays to the site of the weed infestation.

The emulsifiers most commonly used in these concentrates are nonionic or mixtures of nonionic with anionic surface active agents. With the use of some emulsifier systems an inverted emulsion (water in oil) can be prepared for direct application to weed infestions.

A typical herbicidal composition according to this invention is illustrated by the following example, in which the quantities are in parts by weight.

EXAMPLE 17

Preparation of a Dust

Product of Example
Powdered Talc:

The above ingredients are mixed in a mechanical grinder-blender and are ground until a homogeneous, freeflowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB,) 2,4,-DEB, 4-CPB, 4-CPA, 4-CPP, 2,4,5-TB, 2,4,5-TES, 3,4-DA, silvex and the like; carbamate herbicides such as IPC, CIPC, swep barban, BCPC, CEPC, CPPC, and the like; thiocarbamate and dithiocarbamate herbicides such as CDEC, metham sodium, EPTC, diallate, PEBC, perbulate, vernolate and the like, substituted urea herbicides such as norea, siduron, dichloral urea, chloroxurn, cyculron, fenuron, monuron, monuron TCA, diuron, linuron, monlinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloracetamide herbicides such as 4-(chloroacetyl)morpholine, 1-(chloroacetyl)-piperidine and the like; chlorinated aliphtic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS bromacil, 2-(3,4-dichlorophenyl)-4-methyl-1,2,4-oxadiazolidine, 3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sow-thistle, coffeeweed, croton, cuphea, dodder, fumitory, roundsel, hemp nettle, knawel, spurge, spurry, emex, jungle rice, pondweed, dog gennel, carpetweed, morngglory, bedstraw, duchsalad, naiad, cheatgrass, fall panicum, kimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and winter-cress.

Similary, such weeds can be classified as broadleaf or grass weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as per- and post-emergence testing.

The herbicidal activity of the compounds of this invention can be demonstrated by experiments carried out for the pre-emergence control of a variety of weeds. In these experiments small plastic greenhouse pots filled with dry soil are seeded with the various weed seeds. Twenty-four hours or less after seeding the pots are sprayed with water until the soil is wet and a test compound formulated as an aqueous emulsions of acetone solutions containing emulsifiers were sprayed at the indicated concentrations on the surface of the soil.

After spraying, the soil containers are placed in the greenhouse and provided with supplementary heat as required and daily or more frequent watering. The plants are maintained under these conditions for a period of from 14 to 21 days, at which time the condition of the plants and the degree of injury to the plants is rated on a scale of from 0 to 10, as follows: 0=no injury, 1,2=slight injury, 3,4=moderate injury, 5,6=moderately severe injury, 7,8,9=severe injury and 10=death. The effectiveness of these compounds is demonstrated by the data in Table I below.

The herbicidal activity of the compounds of this invention can also be demonstrated by experiments carried out for the post-emergence control of a variety of weeds. In these experiments the compounds to be tested are formulated as aqueous emulsions and sprayed at the desired dosage on the foliage of the weeds that have attained a prescribed size. After spraying the plants are placed in a greenhouse and watered daily or more frequently. Water is not applied to the foliage of the treated plants. The severity of the injury is determined 14 days after treatment and is rated on the scale of from 0 to 10 heretofore described. The effectiveness of these compounds is demonstrated by the data in Table II below.

In both Tables I and II the following abbreviations for the various weed species and crop species were used:
ABLUE—Annual Bluegrass
ALFA—Alfalfa
BDWD—Bindweed
BNGS—Barnyardgrass
CBGS—Crabgrass
CORN—Corn
COTN—cotton
CTGS—Cheatgrass (Downy Brome)
JMWD—Jimsonweed
JNGS—Johnsongrass
MBLUE—Merion Bluegrass
MNGY—Morningglory, Annual
OAT—Oat
PIGW—Pigweed
PTBN—Pintobean
PYRE—Perennial Ryegrass
QKGS—Quackgrass
RICE—Rice
SORG—Sorghum
SOYB—Soybean
SPGT—Sprangletop
SUBT—Sugar Beet
TFES—Tall Fescue
VTLF—Velvetleaf
WHT—Wheat
WMSTD—Wild Mustard
WOAT—Oats, Wild
YLFX—Foxtail, Yellow
YNSG—Nutsedge, Yellow In Tables I and II the term NE is used to designate non-emergence and decimal places are the result of replicate averages.

TABLE I

Injury Rating - Pre-Emergence

| TEST COMPOUND | RATE lbs/Acre | TIME AFTER TREATMENT (Days) | YNSG | WOAT | JMWD | VTLF | JNGS | PIGW | WMSTD | YLFX | BNGS | CBGS | CTGS | MNGY |
|---|---|---|---|---|---|---|---|---|---|---|---|---|---|---|
| Product of Ex. 2 | 8 | 14 | 9 | 4 | 9 | 6 | 9 | 7 | 6 | 10 | 10 | 9 | 10 | 9 |
| " | 2 | 14 | 7 | 3.3 | 6.1 | 4 | 7.3 | 6 | 3.5 | 8.5 | 9 | 8 | 9 | 7.1 |
| " | 1 | 14 | 7.2 | 2.3 | 4.5 | 2 | 5.3 | 5.5 | 1.5 | 8.5 | 9 | 7 | 10 | 5.4 |
| " | 0.5 | 14 | — | 3 | 4.3 | 5.3 | 6.1 | 8.3 | 4 | 8.3 | 10 | 8.3 | 5 | 6 |
| " | 0.25 | 14 | — | 3 | 4.3 | 4.3 | 5.1 | 3 | 4 | 6 | 9.3 | 8.3 | 2 | 3.5 |
| " | 0.125 | 14 | — | 5 | 5 | 5 | 5 | 5 | 3.3 | 7 | 10 | 8 | — | 5 |

| | | | BDWD | MBLUE | TFES | PYRE | SUBT | WHT | RICE | SOYB | COTN | SORG | PTBN | CORN |
|---|---|---|---|---|---|---|---|---|---|---|---|---|---|---|
| " | 8 | 14 | 5 | — | — | — | — | — | — | 3 | 7 | 9 | 5 | — |
| " | 2 | 14 | 3.3 | — | — | — | 9 | NE | 10 | 2.5 | 2 | 9 | 0 | 3 |
| " | 1 | 14 | 7.5 | — | — | — | 6 | NE | 10 | 0.6 | 2 | 9 | 0 | 1 |
| " | 0.5 | 14 | 0 | — | — | — | 0 | 9 | 10 | 5 | 3 | 9 | 0 | 3.2 |
| " | 0.25 | 14 | 0 | — | — | — | 0 | 7 | 10 | 5.3 | — | — | — | 3 |
| " | 0.125 | 14 | — | — | — | — | — | — | — | 6 | — | — | — | 3 |

| | | | OKGS | ALFA | OAT | SPGT | CKBR | | | | | | | |
|---|---|---|---|---|---|---|---|---|---|---|---|---|---|---|
| " | 8 | 14 | 9 | 0 | 4 | 9 | — | | | | | | | |
| " | 2 | 14 | 9 | 0 | 1 | 9 | 4 | | | | | | | |
| " | 1 | 14 | 7 | 0 | 0 | 9 | 3 | | | | | | | |
| " | 0.5 | 14 | 6 | 0 | 0 | — | 7 | | | | | | | |
| " | 0.25 | 14 | — | — | — | — | 6.1 | | | | | | | |
| " | 0.125 | 14 | — | — | — | — | 7 | | | | | | | |

Injury Rating - Pre-Emergence

| TEST COMPOUND | RATE lbs/Acre | TIME AFTER TREATMENT (Days) | YNSG | WOAT | JMWD | VTLF | JNGS | PIGW | WMSTD | YLFX | BNGS | CBGS | CTGS | MNGY |
|---|---|---|---|---|---|---|---|---|---|---|---|---|---|---|
| Product of Ex. 2 | 8 | 21 | 10 | 3 | 9 | 7 | 9 | 10 | 8 | 10 | 10 | 10 | 10 | 10 |
| " | 2 | 21 | NE | 1.6 | 6.4 | 5.8 | 6.4 | 10 | 4 | 9.6 | 10 | 9 | 10 | 7.2 |
| " | 1 | 21 | 9.7 | 0.6 | 4.8 | 3.6 | 4.5 | 7.4 | 1 | 9.2 | 10 | 7 | 10 | 6.5 |
| " | 0.5 | 21 | — | 3.3 | 5.3 | 4.3 | 6.1 | 8.3 | 4 | 8 | 10 | 8 | 9 | 5 |
| " | 0.25 | 21 | — | 3.3 | 4.3 | 4 | 6 | 4 | 2.5 | 6.3 | 10 | 8 | 9.2 | 5 |
| " | 0.125 | 21 | — | 5 | 5 | 6 | 5.2 | 5 | 5 | 8 | 10 | 7 | — | 5 |

| | | | BDWD | MBLUE | TFES | PYRE | SUBT | WHT | RICE | SOYB | COTN | SORG | PTBN | CORN |
|---|---|---|---|---|---|---|---|---|---|---|---|---|---|---|
| " | 8 | 21 | 10 | — | — | — | — | — | — | 3 | 7 | 9 | 5 | — |
| " | 2 | 21 | 7 | — | — | — | 5 | NE | 10 | 1 | 3 | 10 | 1 | 4 |
| " | 1 | 21 | 0 | — | — | — | 5 | NE | 10 | 5 | 1 | 9 | 0 | 2 |
| " | 0.5 | 21 | 0 | — | — | — | 0 | 7 | 10 | 6 | 2 | 8 | 0 | 4 |
| " | 0.25 | 21 | 0 | — | — | — | 0 | 9 | — | 6.3 | — | 7 | — | 5 |
| " | 0.125 | 21 | — | — | — | — | — | — | — | 6.2 | — | — | — | 5 |

| | | | OKGS | ALFA | OAT | SPGT | CKBR | | | | | | | |
|---|---|---|---|---|---|---|---|---|---|---|---|---|---|---|
| " | 8 | 21 | 10 | 2 | 4 | 10 | 4 | | | | | | | |
| " | 2 | 21 | 9 | 1 | 2 | 10 | 3 | | | | | | | |
| " | 1 | 21 | 9 | 0 | 1 | 10 | 6.4 | | | | | | | |
| " | 0.5 | 21 | 7 | 0 | 0 | 9 | 5 | | | | | | | |
| " | 0.25 | 21 | | | | | | | | | | | | |

TABLE I-continued

Injury Rating - Pre-Emergence

| TEST COMPOUND | RATE lbs/Acre | TIME AFTER TREATMENT (Days) | YNSG | WOAT | JMWD | VTLF | JNGS | PIGW | WMSTD | YLFX | BNGS | CBGS | CTGS | MNGY |
|---|---|---|---|---|---|---|---|---|---|---|---|---|---|---|
| Product of Ex. 4 | 8 | 14 | NE | 7 | 8 | 7 | 9 | 10 | 8 | 9 | 10 | 10 | 9 | 8 |
| " | 2 | 14 | NE | 5 | 7 | 6 | 9 | 10 | 7 | 9 | 10 | 9 | 10 | 6 |
| " | 1 | 14 | NE | 3 | 6 | 4.3 | 7 | 10 | 6 | 9 | 10 | 9 | 10 | 4 |
| " | 0.5 | 14 | — | 0 | 4 | 6 | 5 | 9 | 0 | 5 | 10 | 8 | NE | 3 |
| " | 0.25 | 14 | — | 0 | 2 | 4 | 5 | NE | 0 | 4 | 9 | 6 | NE | 1 |
| " | 0.125 | 14 | — | — | — | — | — | — | — | — | — | — | — | — |

| | | | BDWD | MBLUE | TFES | PYRE | SUBT | WHT | RICE | SOYB | COTN | SORG | PTBN | CORN |
|---|---|---|---|---|---|---|---|---|---|---|---|---|---|---|
| " | 8 | 14 | — | — | — | — | 1 | NE | NE | 1 | 5 | 8 | 0 | 3 |
| " | 2 | 14 | 0 | 2 | — | — | 1 | NE | NE | 1 | 3 | 7 | 0 | 0 |
| " | 1 | 14 | 0 | 1 | — | — | — | NE | NE | 0 | NE | 5 | 0 | 0 |
| " | 0.5 | 14 | 2 | 0 | — | — | 3 | NE | NE | 0 | 1 | 3 | 0 | 0 |
| " | 0.25 | 14 | 0 | 0 | — | — | 0 | 3 | NE | — | — | — | — | — |
| " | 0.125 | 14 | — | — | — | — | — | — | — | — | — | — | — | — |

| | | | OKGS | ALFA | OAT | SPGT |
|---|---|---|---|---|---|---|
| " | 8 | 14 | — | 2 | NE | — |
| " | 2 | 14 | NE | 1 | 2 | NE |
| " | 1 | 14 | NE | 0 | 2 | NE |
| " | 0.5 | 14 | NE | 0 | 0 | 9 |
| " | 0.25 | 14 | NE | — | — | 9 |
| " | 0.125 | 14 | — | — | — | — |

Injury Rating - Pre-Emergence

| TEST COMPOND | RATE lbs/Acre | TIME AFTER TREATMENT (Days) | YNSG | WOAT | JMWD | VTLF | JNGS | PIGW | WMSTD | YLFX | BNGS | CBGS | CTGS | MNGY |
|---|---|---|---|---|---|---|---|---|---|---|---|---|---|---|
| Product of Ex. 4 | 8 | 21 | NE | 5 | 7 | 8 | 10 | 10 | 8 | 9 | 10 | 10 | 10 | 7 |
| " | 2 | 21 | NE | 4 | 4 | 8 | 9 | 9 | 5 | 9 | 10 | 9 | 10 | 4 |
| " | 1 | 21 | NE | 4 | 5 | 7 | 5 | 9 | 3 | 8 | 10 | 8 | 10 | 4 |
| " | 0.5 | 21 | — | 4 | 1 | — | — | 7 | 1 | 5 | 10 | 6 | NE | 3 |
| " | 0.25 | 21 | — | 0 | 0 | — | — | NE | 0 | 3 | 10 | 3 | NE | 1 |
| " | 0.125 | 21 | — | — | — | — | — | — | — | — | — | — | — | — |

| | | | BDWD | MBLUE | TFES | PYRE | SUBT | WHT | RICE | SOYB | COTN | SORG | PTBN | CORN |
|---|---|---|---|---|---|---|---|---|---|---|---|---|---|---|
| " | 8 | 21 | 1 | — | — | — | 0 | NE | — | — | — | 8 | 0 | 2 |
| " | 2 | 21 | 0 | — | — | — | 0 | NE | — | — | — | 6 | 0 | 0 |
| " | 1 | 21 | 4 | — | — | — | 6 | NE | — | — | — | 3 | 0 | 0 |
| " | 0.5 | 21 | 0 | — | — | — | 0 | 2 | — | — | — | 3 | 0 | 0 |
| " | 0.25 | 21 | — | — | — | — | — | — | — | — | — | — | — | — |
| " | 0.125 | 21 | — | — | — | — | — | — | — | — | — | — | — | — |

| | | | OKGS | ALFA | OAT | SPGT |
|---|---|---|---|---|---|---|
| " | 8 | 21 | — | 2 | NE | 10 |
| " | 2 | 21 | 9 | 3 | 2 | NE |
| " | 1 | 21 | 10 | — | — | — |

TABLE I-continued

| TEST COMPOUND | RATE lbs/Acre | TIME AFTER TREATMENT (Days) | YNSG | WOAT | JMWD | VTLF | JNGS | PIGW | WMSTD | YLFX | BNGS | CBGS | CTGS | MNGY |
|---|---|---|---|---|---|---|---|---|---|---|---|---|---|---|
| " | 0.5 | 21 | — | 9 | 0 | 0 | 10 | — | — | — | — | — | — | 5 |
| " | 0.25 | 21 | — | 8 | 0 | 0 | 10 | — | — | — | — | — | — | 2 |
| " | 0.125 | 21 | — | — | — | — | — | — | — | — | — | — | — | 2 |

Injury Rating - Pre-Emergence

Weed Species

| TEST COMPOUND | RATE lbs/Acre | TIME AFTER TREATMENT (Days) | YNSG | WOAT | JMWD | VTLF | JNGS | PIGW | WMSTD | YLFX | BNGS | CBGS | CTGS | MNGY |
|---|---|---|---|---|---|---|---|---|---|---|---|---|---|---|
| Product of Ex. 13 | 8 | 14 | NE | 6 | 5 | 4 | 8 | 9 | 3 | 9 | 10 | NE | NE | — |
| " | 2 | 14 | NE | 3 | 2 | 4 | 7 | 6 | 3 | 9 | 9 | NE | NE | — |
| " | 1 | 14 | NE | 2 | 2 | 4 | 7 | 3 | 1 | 7 | 10 | 5 | 4 | — |
| " | 0.5 | 14 | — | — | — | — | — | — | — | — | — | — | — | — |
| " | 0.25 | 14 | — | — | — | — | — | — | — | — | — | — | — | — |
| " | 0.125 | 14 | — | — | — | — | — | — | — | — | — | — | — | — |
| " | 8 | 21 | NE | 6 | 4 | 5 | 10 | 10 | 2 | 10 | 10 | NE | NE | 3 |
| " | 2 | 21 | 7 | 3 | 2 | 5 | 8 | 4 | 2 | 8 | 10 | 8 | NE | 1 |
| " | 1 | 21 | 5 | 1 | 0 | 4 | 5 | 2 | 2 | 8 | 10 | 7 | 4 | 1 |
| " | 0.5 | 21 | — | — | — | — | — | — | — | — | — | — | — | — |
| " | 0.25 | 21 | — | — | — | — | — | — | — | — | — | — | — | — |
| " | 0.125 | 21 | — | — | — | — | — | — | — | — | — | — | — | — |

TABLE II

Injury Rating - Post-Emergence

| TEST COMPOUND | RATE lbs/Acre | TIME AFTER TREATMENT (Days) | Weed Species | | | | | | | | | | | |
|---|---|---|---|---|---|---|---|---|---|---|---|---|---|---|
| | | | YNSG | WOAT | JMWD | VTLF | JNGS | PIGW | WMSTD | YLFX | BNGS | CBGS | CTGS | MNGY |
| Product of Ex. 2 | 8 | 14 | — | — | — | — | — | — | — | — | — | — | — | — |
| " | 2 | 14 | — | 4 | 8 | 3 | 9 | 6 | 2 | 8 | 9 | 8 | 6 | 9 |
| " | 1 | 14 | — | 5 | 6 | 2 | 7 | 2 | 1 | 8 | 9 | 8 | 3 | 9 |
| " | 0.5 | 14 | — | 3 | 4 | 1 | 6 | 2 | 0 | 8 | 9 | 6 | 1 | 7 |
| " | 0.25 | 14 | — | 2 | 3 | 1 | 3 | 1 | 0 | 7 | 8 | 3 | 0 | 5 |
| " | 0.125 | 14 | — | — | — | — | — | — | — | — | — | — | — | — |

| TEST COMPOUND | RATE lbs/Acre | TIME AFTER TREATMENT (Days) | BDWD | MBLUE | TFES | PYRE | SUBT | WHT | RICE | SOYB | COTN | SORG | PTBN | CORN |
|---|---|---|---|---|---|---|---|---|---|---|---|---|---|---|
| " | 8 | 14 | — | — | — | — | — | — | — | — | — | — | — | — |
| " | 2 | 14 | 3 | — | — | — | 3 | 7 | 4 | 4 | 1 | 4 | 3 | 2 |
| " | 1 | 14 | 1 | — | — | — | 1 | 6 | 4 | 3 | 2 | 3 | 0 | 2 |
| " | 0.5 | 14 | 0 | — | — | — | 0 | 6 | 5 | 4 | 3 | 2 | 0 | 0 |
| " | 0.25 | 14 | 0 | — | — | — | 0 | 1 | 3 | 9 | 2 | 0 | 0 | 0 |
| " | 0.125 | 14 | — | — | — | — | — | — | — | — | — | — | — | — |

| TEST COMPOUND | RATE lbs/Acre | TIME AFTER TREATMENT (Days) | OKGS | ALFA | OAT | SPGT |
|---|---|---|---|---|---|---|
| " | 8 | 14 | — | — | — | — |
| " | 2 | 14 | 8 | 4 | 4 | 7 |
| " | 1 | 14 | 7 | 0 | 2 | 7 |
| " | 0.5 | 14 | 7 | 0 | 1 | 6 |
| " | 0.25 | 14 | 6 | 0 | 0 | 6 |
| " | 0.125 | 14 | — | — | — | — |

I claim:

1. A compound of the formula

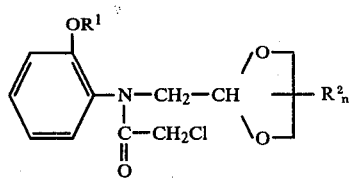

wherein $R^1$ and $R^2$ are each independently methyl, ethyl or propyl and n is the integer 1 or 2.

2. The compound of claim 1, N-(4,5-dimethyl-1,3-dioxolan-2-ylmethyl)-2-methoxy-α-chloroacetanide.

3. The compound of claim 1, N-(4-methyl-1,3-dioxolan-2-ylmethyl)-2-methoxy-α-chloroacetamide.

4. The compound of claim 1, N-(4-ethyl-1,3-dioxolan-2-ylmethyl)-2-methoxy-α-chloroacetamide.

5. The compound of claim 1, N-(4,5-diethyl-1,3-dioxolan-2-ylmethyl)-2-methoxy-α-chloracetamide.

6. The compound of claim 1, N-(4-methyl-5-ethyl-1,3-dioxolan-2ylmethyl)-2-methoxy-α-chloroacetamide.

7. The compound of claim 1, N-(4,5-dimethyl-1,3-dioxolan-2-ylmethyl)-2-ethoxy-α-chloroacetamide.

8. The compound of claim 1, N-(4-ethyl-1,3-dioxolan-2-ylmethyl)-2-ethoxy-α-chloroacetamide.

9. A herbicidal composition comprising an inert carrier and as an essential active ingredient, in a quantity toxic to weeds, a compound of claim 1.

10. A method of controlling weeds which comprises contacting the locus of said weeds with a herbicidal composition comprising an inert carrier and, as an essential active ingredient, in a quantity toxic to said weeds, a compound of claim 1.

* * * * *